US011941842B2

(12) United States Patent
Rongen et al.

(10) Patent No.: US 11,941,842 B2
(45) Date of Patent: Mar. 26, 2024

(54) DEVICE, SYSTEM AND METHOD FOR DETERMINING THE POSITION OF STENTS IN AN IMAGE OF VASCULATURE STRUCTURE

(71) Applicant: KONINKLIJKE PHILIPS N.V., Eindhoven (NL)

(72) Inventors: Peter Maria Johannes Rongen, Eindhoven (NL); Markus Johannes Harmen Den Hartog, Eindhoven (NL); Javier Olivan Bescos, Eindhoven (NL); Thijs Elenbaas, Nijmegen (NL); Iris Ter Horst, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 909 days.

(21) Appl. No.: 16/966,389

(22) PCT Filed: Jan. 28, 2019

(86) PCT No.: PCT/EP2019/051933
§ 371 (c)(1),
(2) Date: Jul. 30, 2020

(87) PCT Pub. No.: WO2019/149639
PCT Pub. Date: Aug. 8, 2019

(65) Prior Publication Data
US 2020/0372674 A1 Nov. 26, 2020

(30) Foreign Application Priority Data

Jan. 31, 2018 (EP) .................................... 18154357

(51) Int. Cl.
G06Q 30/0601 (2023.01)
A61B 6/12 (2006.01)
(Continued)

(52) U.S. Cl.
CPC .................. *G06T 7/74* (2017.01); *A61B 6/12* (2013.01); *A61B 6/504* (2013.01); *A61B 8/0841* (2013.01);
(Continued)

(58) Field of Classification Search
CPC . G06T 7/74; G06T 5/001; G06T 2207/10016; G06T 2207/10116;
(Continued)

(56) References Cited

U.S. PATENT DOCUMENTS 8,473,030 B2 6/2013 Greenan et al.
2005/0155184 A1 7/2005 Kayl
(Continued)

FOREIGN PATENT DOCUMENTS

EP 1363558 B1 11/2009
EP 3200150 A1 8/2017
(Continued)

OTHER PUBLICATIONS

Agostoni et al: "Bifurcation Stenting With a Dedicated Biolimus-Eluting Stent:X-Ray Visual Enhancement of the Final Angiographical Result With Stentboost Substract"; Coronary Artery Disease, Mar. 2007.
(Continued)

*Primary Examiner* — Amara Abdi

(57) ABSTRACT

The present invention relates to a device (10) for determining the position of stents (34, 36) in an image of vasculature structure, the device (10) comprising: an input unit (12); a processing unit (14); and an output unit (16); wherein the input unit (12) is configured to receive a sequence of images (24) of a vasculature structure (38) comprising at least one vessel branch (44, 46); wherein the processing unit (14) is configured to: detect positions of at least two markers (26, 28, 30, 32) for identifying a stent position (50, 52) in at least (Continued)

one of the images (24); detect at least one path indicator (64, 66, 74, 76) for the at least one vessel branch (44, 46) in at least one of the images (24) of the vasculature structure (38) at least for vessel regions in which the positions of the markers (26, 28, 30, 32) are detected; associate the at least two markers (26, 28, 30, 32) to the at least one path indicator (64, 66, 74, 76) based on the detected positions of the markers (26, 28, 30, 32) and the location of the at least one path indicator (64, 66, 74, 76); assign markers (26, 28, 30, 32) which are associated to the same path indicator (64, 66, 74, 76) to a marker group to indicate a position (50, 52) of at least one stent (34, 36) in the vasculature structure (38); and wherein the output unit (16) is configured to provide output data indicative of the positions of the markers (26, 28, 30, 32) of the marker group. The invention provides a device and a method that improve the determination of the position of stents in complicated situations.

20 Claims, 3 Drawing Sheets

(51) Int. Cl.
*A61B 6/50* (2024.01)
*A61B 8/08* (2006.01)
*A61F 2/82* (2013.01)
*G06T 5/00* (2006.01)
*G06T 7/73* (2017.01)

(52) U.S. Cl.
CPC ............... *A61F 2/82* (2013.01); *G06T 5/001* (2013.01); *A61F 2250/0098* (2013.01); *G06T 2207/10016* (2013.01); *G06T 2207/10116* (2013.01); *G06T 2207/10132* (2013.01); *G06T 2207/30101* (2013.01); *G06T 2207/30204* (2013.01)

(58) Field of Classification Search
CPC . G06T 2207/10132; G06T 2207/30101; G06T 2207/30204; G06T 2207/30172; A61B 6/12; A61B 6/504; A61B 8/0841; A61B 6/487; A61B 8/0891; A61B 6/486; A61F 2/82; A61F 2250/0098
See application file for complete search history.

(56) References Cited

U.S. PATENT DOCUMENTS

| | | | |
|---|---|---|---|
| 2006/0155184 A1* | 7/2006 | Florent | G06T 7/12 |
| | | | 600/407 |
| 2007/0203562 A1 | 8/2007 | Malewicz et al. | |
| 2007/0260217 A1 | 11/2007 | Von Oepen et al. | |
| 2008/0147174 A1 | 6/2008 | Konstantino et al. | |
| 2010/0161023 A1 | 6/2010 | Cohen et al. | |
| 2012/0302876 A1* | 11/2012 | Van Stevendaal | A61B 6/547 |
| | | | 382/103 |
| 2013/0301897 A1* | 11/2013 | Zhu | G06T 5/50 |
| | | | 382/132 |
| 2014/0241599 A1* | 8/2014 | Chen | A61B 5/0036 |
| | | | 382/128 |
| 2017/0213343 A1* | 7/2017 | Vaillant | A61B 6/12 |
| 2017/0231646 A1* | 8/2017 | Epstein | A61B 17/221 |
| | | | 606/200 |

FOREIGN PATENT DOCUMENTS

| | | |
|---|---|---|
| JP | 2015150049 A | 8/2015 |
| JP | 2017131634 A | 8/2017 |
| WO | 03045263 A2 | 6/2003 |
| WO | 2008050315 A2 | 5/2008 |

OTHER PUBLICATIONS

Fysal et al: "Evaluating Stent Optimisation Technique (Stentboost) in a Dedicated Bifurcation Stent (The Tryton)"; Cardiovascular Revascularization Medicine 15 (2014), pp. 92-96.
Koninklijke Philips N.V. : "A Unique Cardiovascular Offering Across the Entire Care Conintuum", 2007, 16 Page Document.
PCT/EP2019/051933 ISR & WO, dated Mar. 7, 2019, 16 pages.

* cited by examiner

DEVICE, SYSTEM AND METHOD FOR DETERMINING THE POSITION OF STENTS IN AN IMAGE OF VASCULATURE STRUCTURE

CROSS-REFERENCE TO PRIOR APPLICATIONS

This application is the U.S. National Phase application under 35 U.S.C. § 371 of International Application No PCT/EP2019/051933, filed on Jan. 28, 2019, which claims the benefit of European Patent Application No. 18154357.0, filed on Jan. 31, 2018. These applications are hereby incorporated by reference herein.

FIELD OF THE INVENTION

The present invention relates to a device, a system and a method for determining the position of stents in an image of vasculature structure.

BACKGROUND OF THE INVENTION

In percutaneous coronary interventions, it is of importance that a coronary stent is fully expanded and in full contact with the coronary vessel wall after placement in a coronary stenotic lesion. Furthermore, correct positioning of the stent with respect to side branches of the vessel is crucial, especially when stenting a coronary bifurcation. A stent is not always clearly visible under fluoroscopy or in an exposure run. Improvement of stent visibility in X-ray exposure thus facilitates the interventional cardiologist to correctly place the stent and in judging the clinical success of the intervention.

There are some complicated situations in which stents in different vessels of a bifurcated vessel structure overlap. In those situations, an improvement of the stent visibility cannot be performed since the stents cannot be correctly detected.

U.S. Pat. No. 8,473,030 B2 describes a prosthesis deployment apparatus using a real-time monitoring method for monitoring the position of a vessel branching from another vessel. First a multi-dimensional data set of a portion of the vessels is acquired. Then, at least one marker is secured to the vessels near the branch-off. The position of the marker is determined in real-time. Then, the position of a portion of the multi-dimensional data set is updated based on the position of the marker. This method determines the location and/or the orientation of a vessel or a vessel branch prior or during a prosthesis deployment. However, a determination of the location of several stents may not be performed with this method.

SUMMARY OF THE INVENTION

There may thus be a need to provide a device and a method that improve the determination of the position of stents in complicated situations.

The object of the present invention is solved by the subject-matter of the independent claims; further embodiments are incorporated in the dependent claims. It should be noted that the following described aspects of the invention apply also for the system, the method, the computer program element, and the computer readable medium.

According to the present invention, a device for determining the position of stents in an image of vasculature structure is provided. The device comprises an input unit; a processing unit; and an output unit; wherein the input unit is configured to receive a sequence of images of a vasculature structure comprising at least one vessel branch; wherein the processing unit is configured to: detect positions of at least two markers for identifying a stent position in at least one of the images; detect at least one path indicator for the at least one vessel branch in at least one of the images of the vasculature structure at least for vessel regions in which the positions of the markers are detected; associate the at least two markers to the at least one path indicator based on the detected positions of the markers and the location of the at least one path indicator; assign markers which are associated to the same path indicator to a marker group to indicate a position of at least one stent in the vasculature; and wherein the output unit is configured to provide output data indicative of the positions of the markers of the marker group.

The image of vasculature structure comprises at least one vessel branch in which a stent may be positioned. The stent may be detected using at least two markers which are located at the position of the stent. The position of those at least two markers may be detected in the image of vasculature structure by the processing unit.

The processing unit may further detect at least one path indicator in at least one of the image of vasculature structures of the sequence. The path indicator indicates a path along the at least one vessel branch in the region in which the markers have been detected. Based on the path indicator, the processing unit determines the position of the vessel branch in the image of vasculature structure. In an example, the path indicator may be determined prior to receiving an image of vasculature structure which shows stents and markers. In that example, the processing unit will detect the path indicator for the whole vessel branch and later extract the vessel region in which the markers are found.

After detecting the path indicators and thus the position of the vessel branches, the processing unit compares the positions of the markers with the location and extension of one or more vessel branches. If the comparison confirms that the position of two or more markers correspond to the same vessel branch, the respective markers are subsequently associated with the respective path indicator.

The processing unit thus groups all markers into a marker group which are associated to the same path, i.e. which are arranged in the vessel branch. A marker group or pair may determine the position of the stent in the image of vasculature structure. Since the markers of a marker group each are arranged on the same path, a marker group determines the position of a single stent in the image of vasculature structure.

Thus, according to the present invention the markers can be associated to the correct stents such that stent positions may be consistently determined. Furthermore, the consistency of existing determined stent positions can be checked. This provides an improved determination of stents in complicated situations.

In an example, the processing unit may select at least one preliminary marker group before detecting the path indicators. This means that the processing unit will check the consistency of the selection according to the above description.

In an example, the device is used during a percutaneous coronary intervention (PCI).

In an example, the marker group comprises two markers.

The term "marker for identifying a stent position" relates to a marker that is indicative of a possible position of a stent. The markers can also be referred to as "stent markers". However, it must be noted that the markers can be provided on the stent itself or also not on the stent itself but provided separately on a stent element, e.g. on a balloon or another device used for stent positioning.

In an example, the vessel branch is detected from an angiogram, i.e. a contrast enhanced image, and the wire is detected from a non-contrast-enhanced image since in an angiogram, the contrast filled vessel obscures the wire. In an example, the marker positions are detected from a non-contrast-enhanced image.

In an example, a sequence of images including both contrast-enhanced and non-contrast-enhanced images is provided.

According to an example, the input unit is configured to receive a sequence of images of a vasculature structure comprising at least two vessel branches; wherein the processing unit is configured to: detect positions of at least three markers for identifying a stent position; and detect path indicators for the at least two vessel branches in at least one of the images of the vasculature structure at least for vessel regions in which the positions of the markers are detected; associate the at least three markers to the path indicators based on the detected positions of the markers and the location of the path indicators; and assign markers which are associated to the same path indicator to a marker group to indicate positions of at least two stents in the vasculature.

In that example, the image of vasculature structure comprises at least two vessel branches in which the stents are positioned. One stent is arranged in one vessel branch, another stent in the other vessel branch. The at least two stents may overlap close to the bifurcation of the vessel branches.

Each stent may be located using at least two markers, i.e. with two stents in the image there are at least four markers. In the image of vasculature structure, two markers may overlap which are positioned on different stents since close to the bifurcation the stents may be arranged on the same position in the image of vasculature structure. Thus, in an image having four markers at least three markers may be visible in the image. The position of those at least three markers may be detected in the image by the processing unit.

The processing unit may further detect at least two path indicators in the image of vasculature structure. Each path indicator indicates a path along one of the at least two vessel branches. Based on the path indicators, the processing unit determines the vessel branches. In an example, the path indicators may be defined in a separate image of vasculature structure prior to receiving the image of vasculature structure showing the stents and the markers.

After detecting the path indicators and thus the vessel branches, the processing unit compares the positions of the markers with the extension of the vessel branches. If the comparison results that the position of a marker and a path are positioned in the same vessel branch, the respective marker is associated to the respective path indicator. A marker may be associated to several path indicators, for example if the vessels intersect each other and the marker is positioned at the intersection.

The processing unit groups all markers into a marker group which are associated to the same path, i.e. which are arranged in the same vessel branch. A marker group determines the position of a stent in the image. Since the markers of a marker group each are arranged on the same path, a marker group determines the position of a stent in the image.

Thus, according to the present invention the markers can be associated to the correct stents such that stent positions may be consistently determined. Furthermore, the consistency of existing determined stent positions can be checked. This provides an improved determination of stents in complicated situations.

According to an example, the device further comprises an image enhancement module for further image processing; wherein the output data is provided to the image enhancement module; and wherein the image enhancement module is configured to provide stent enhancement for the at least one stent in at least a part of the sequence of images to provide a stent enhanced image.

The stent enhancement is also referred to as stent boosting. The stent enhanced image is also referred to as stent boost image.

For example, WO 2003/043516 describes an image enhancement concerning the stents shown in the image. The image enhancement is known as StentBoost (trademark of Koninklijke Philips N.V.).

According to an example, the device further comprises a display; wherein the display is configured to display the enhanced stent boost image.

In an example, boosting may mean a change of contrast, bordering the stents, and/or a change of color.

According to an example, for detecting the at least one path indicator, the processing unit is configured to: detect at least one wire and/or guide wire in the at least one of the images of the vasculature structure that connects markers as the at least one path indicators.

For detecting two path indicators, the processing unit is configured to detect at least two wires and/or guide wires in the image of the vasculature structure that connect positions markers as the path indicators.

According to an example, for detecting the at least one path indicator, the processing unit is configured to: detect at least one separate vessel branch in the at least one of the images of the vasculature structure as the at least one path indicator; and/or detect at least one segmented vessel feature for the at least one separate vessel branch in the at least one of the images of the vasculature structure as the at least one path indicator.

In an example, the contrasted bifurcated vasculature is a priori contrasted before a stent is introduced into that vasculature, i.e. before the image of bifurcated vasculature with at least two stents in two different vessel branches is received.

In an example, the segmented vessel feature is a vessel centerline as determined from an angiogram.

According to an example, the processing unit is further configured to detect at least two stent elements in the image of bifurcated vasculature that extend in different vessel branches and that connect the positions of two of the at least two markers as path indicator.

According to an example, the stent element is a balloon.

According to the present invention, also a system for enhancing the images of stents in an image of vasculature structure is provided, the system comprising: an image acquisition device; and a device for determining the position of stents in an image of vasculature structure according to the preceding description; wherein the image acquisition device is configured to acquire and provide the sequence of images of the vasculature structure.

In an example, the processing unit is configured to indicate the marker group in real-time during a PCI.

According to an example, the image acquisition device is: an ultrasound device; or an X-ray image acquisition device, preferably an angiography device.

According to the present invention, also a method for determining the position of stents in an image of vasculature structure is provided, the method comprising the following steps: a) detecting positions of at least two markers for identifying a stent position in at least one of the images; b) detecting at least one path indicator for the at least one vessel branch in at least one of the images of the vasculature structure at least for vessel regions in which the positions of the markers are detected; c) associating the at least two markers to the at least one path indicator based on the detected positions of the markers and the location of the at least one path indicator; d) assigning markers which are associated to the same path indicator to a marker group to indicate a position of at least one stent in the vasculature; and e) providing output data indicative of the positions of the markers of the marker group.

In an example, for detecting the at least one path indicator, it is provided: d1) detecting at least one wire and/or guide wire in the image of the vasculature structure that connects markers as the at least one path indicators; and/or d2) detecting at least one separate vessel branch in the image of the vasculature structure as the at least one path indicator; and/or d3) detecting at least one segmented vessel feature for the at least one separate vessel branch in the image of the vasculature structure as the at least one path indicator.

According to the present invention, also a computer program element for controlling a device according to the above description or system according to the above description is provided, which, when being executed by a processing unit, is adapted to perform the method steps according to the above description.

According to the present invention, also a computer readable medium having stored the program element according to the above description is provided.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
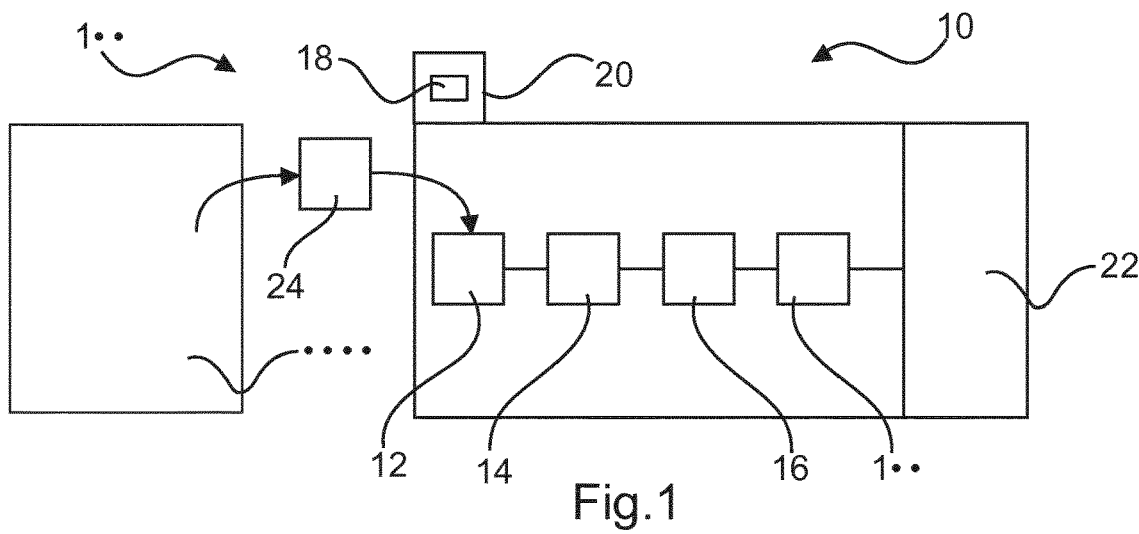
FIG. 1 shows a schematic drawing of the system.

FIG. 1 shows a system 15 for enhancing stent images in an image of vasculature structure. The system 15 comprises an image acquisition device 11 and a device 10 for determining the position of stents 34, 36 in an image of vasculature structure.

The image acquisition device 11 acquires a sequence of images 24 of the vasculature structure 38. In one exemplary embodiment, the image acquisition device 11 may be an ultrasound device. In another exemplary embodiment, the image acquisition device 11 X-ray image acquisition device, preferably an angiography X device. Moreover, the image acquisition device 11 may be any image acquisition device which can acquire images of vasculature structure 38.

In one exemplary embodiment, the image 24 of vasculature structure 38 comprises at least one vessel branch 44, 46. In another exemplary embodiment, the image 24 of vasculature structures 38 comprises at least two vessel branches 44, 46.

The vessel branches 44, 46 may comprise stents 34, 36. However, the stents 34, 36 may be hardly visible in the image 24 of vasculature structure 38.

The image acquisition device 11 provides the sequence of images 24 of the vasculature structure 38 to the device 10 for determining the position of stents 34, 36 in an image of vasculature structure.

Markers 26, 28, 30, 32 which are visible in the image of vasculature structure are arranged at or close to the stents 34, 36. The markers 26, 28, 30, 32 may be arranged on the stents 34, 36 or on stent elements of the stents 34, 36, e.g. on balloons being connected to the stents 34, 36. Furthermore, the markers 26, 28, 30, 32 may be radiopaque.

The device 10 comprises an input unit 12 for receiving the provided sequence of images 24 of vasculature structure 38. Furthermore, the device 10 may comprise a processing unit 14, an output unit 16, an image enhancement module 13, and a display 22.

The processing unit 14 searches the sequence of images 24 to detect the positions of at least two markers 26, 28, 30, 32 for identifying a stent position 50, 52 in at least one of the images 24. This search process is shown in FIGS. 2a to 2d. The result of that search process is shown in FIG. 2e.

Figures 2A, 2B:
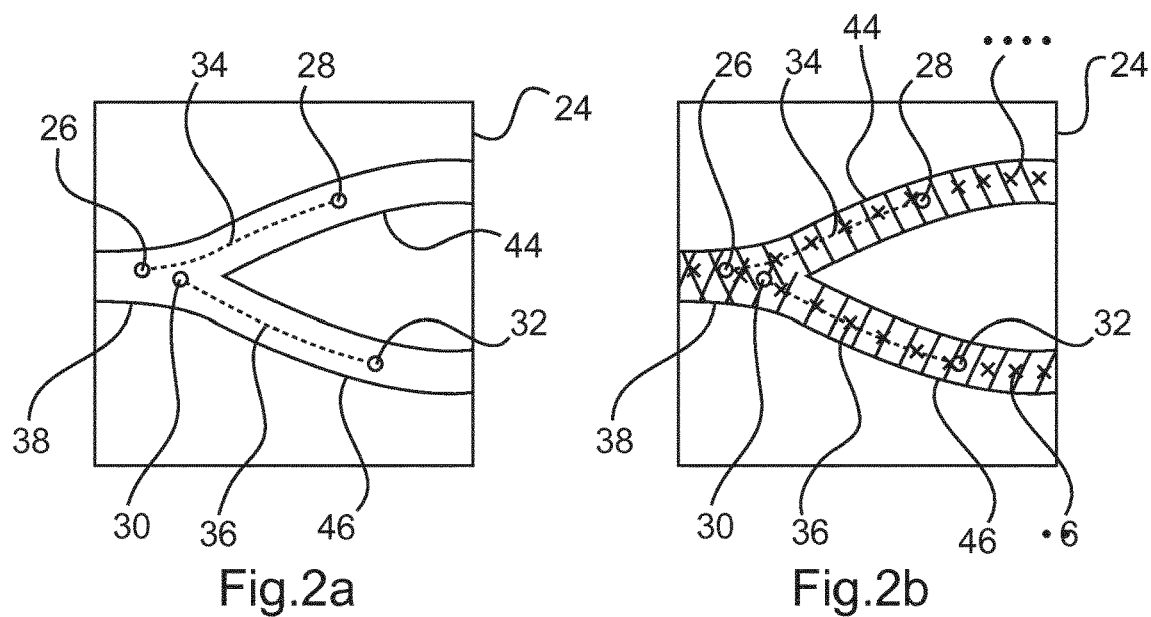
FIG. 2a-e show schematic drawings of images of vasculature structure showing the stent detection process.

FIG. 2a shows an image 24 of the vasculature structure 38 comprising two vessel branches 44, 46. The image 24 is provided by the image acquisition device 11. Each vessel branch 44, 46 comprises a stent 34, 36. Markers 26, 28, 30, 32 are associated to the stents 34, 36. Markers 26 and 28 are located on stent 34 and markers 30 and 32 are located on stent 36.

In an exemplary embodiment, the processing unit 14 may preliminary group the markers 26, 28, 30, 32 immediately after the detection, wherein each group refers to a preliminary position of a stent 34, 36. In this embodiment, the processing unit 14 will then provide a consistency check whether those preliminary positions are consistent with the vasculature structure 38 since there may be the case that markers 28 and 32 are preliminary grouped such that a position of a non-existing stent between the markers 28 and 32 would be determined. However, in another exemplary embodiment, the processing unit 14 will not determine a preliminary position of the stents 34, 36 from the markers 26, 28, 30, 32 and directly start with the detecting the path indicators 64, 66, 74, 76.

Figure 4:
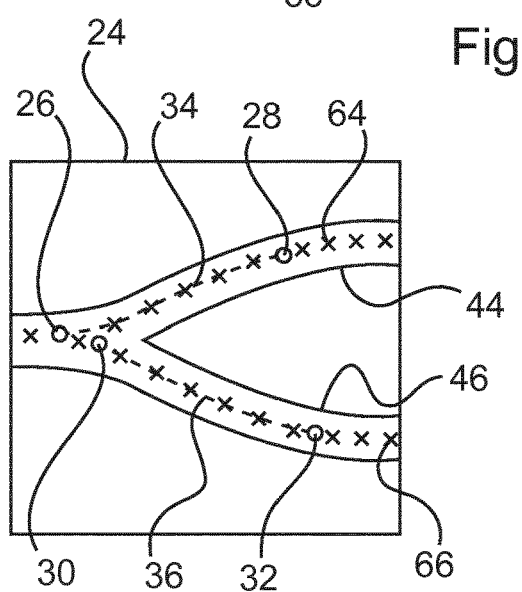
FIG. 4 shows a schematic drawing of an image of vasculature structure with guidewires.
Figure 5:
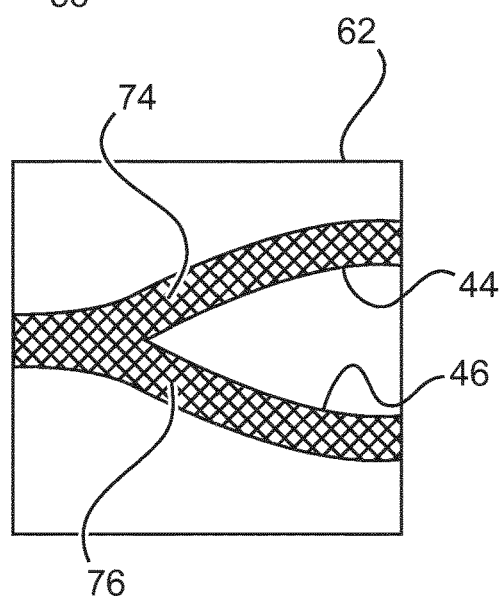
FIG. 5 shows a schematic drawing of an image of contrasted vasculature structure.

The processing unit 14 is configured to detect at least one path indicator 64, 66, 74, 76 for the at least one vessel branch 44, 46. A path indicator 64, 66, 74, 76 indicates a path along the vessel branch 44, 46. This means, the path indicators 64, 66, 74, 76 provide a position of a vessel branch 44, 46 in the image 24 of the vasculature structure 38. Examples of path indicators 64, 66, 74, 76 are shown in FIGS. 4 and 5 and will be discussed in detail below.

In FIG. 2b, a first exemplary embodiment of the path indicators 64, 66, 74, 76 is shown as wires of guidewires which are the path indicators 64 and 66. Those wires or guidewires are shown as a line of crosses along the vessel branches 44, 46. The paths which are indicated by the path indicators 64, 66 are shown in FIG. 2b as single hatching patterns along the vessel branches 44, 46. In the region where the paths cross or overlap, i.e. at the bifurcation of the vasculature structure 38, the two hatching patterns form a cross hatch. The processing unit 14 searches at least the region for the path indicators 64, 66, 74, 76 in which the markers 26, 28, 30, 32 are detected.

After identifying the position of the vessel branches 44 and 46 with the path indicators 64, 66, 74, 76, the processing unit 14 correlates the markers 26, 28, 30, 32 with the vessel branches 44 and 46. According to FIG. 2*b*, markers 26 and 28 are associated with the paths, i.e. the path indicators 64, 66, 74, 76 which indicate the path in the vessel branch 44. Markers 30 and 32 are associated with the path indicator 64, 66, 74, 76 which indicate the path and the vessel branch 46. Moreover, also marker 26 may be associated to the path indicators 64, 66, 74, 76 which indicate the path and the vessel branch 46 since marker 26 is in the overlapping region which is covered by both paths of the vessel branches 44, 46.

Figures 2C, 2D:
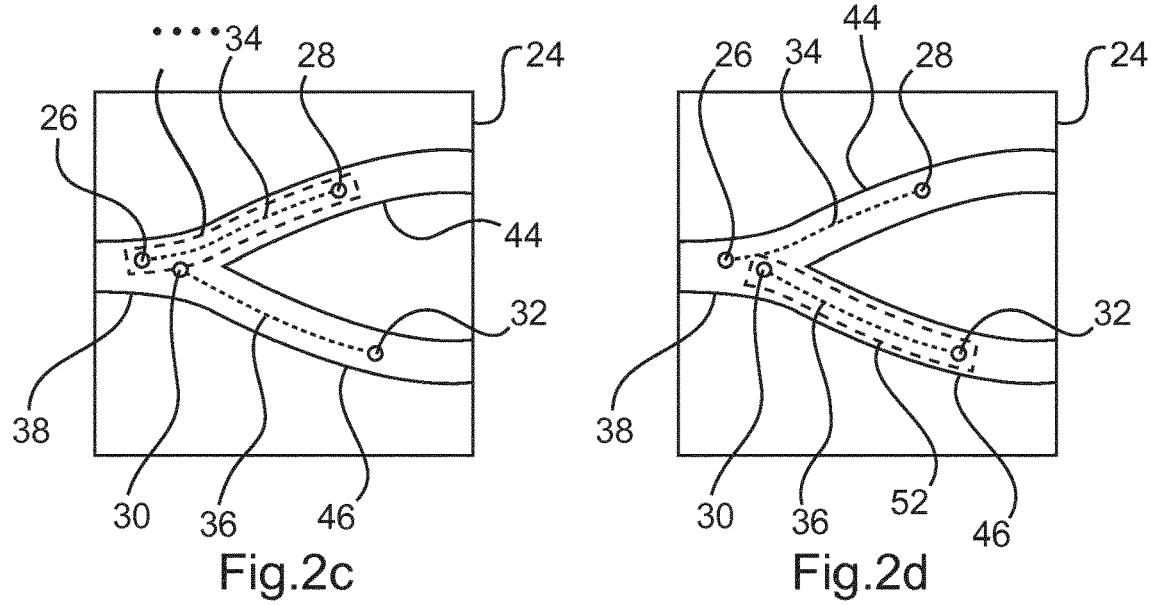
Figure 2E:
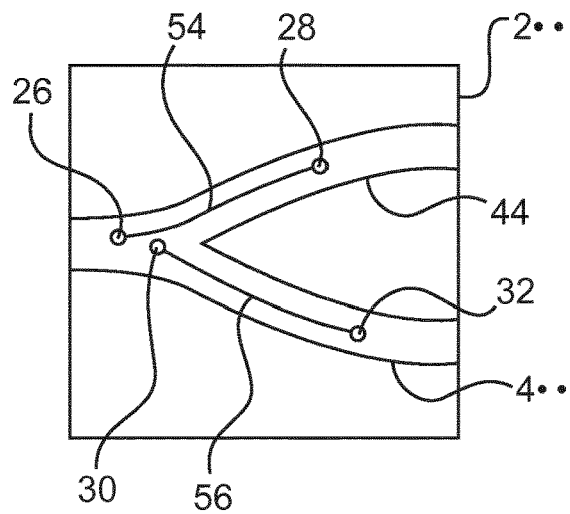

According to FIG. 2*c*, the processing unit 14 groups markers 26 and 28 which are associated with the same path indicators 64, 66, 74, 76 into a marker group. This marker group comprising the markers 26 and 28 indicates the stent position 50 of stent 34.

Moreover, according to FIG. 2*d*, markers 30 and 32 are grouped into a marker group by the processing unit 14 and indicate the stent position 52 of stent 36. In an exemplary embodiment, the processing unit 14 may further be configured to leave out marker 26 from that marker group indicating the stent position 52 since marker 26 is already part of the marker group indicating the stent position 50. Furthermore, a portion of each stent 34, 36 is arranged in the bifurcation of the vasculature structure 38. This means, that markers 26 and 30 are close to each other. In some exemplary cases, those markers 26 and 30 may overlap such that they appear to be one single marker. In that exemplary case the processing unit 14 may associate the single marker in the bifurcation to more than one marker group.

The output unit 16 provides output data indicative of the positions of the markers 26, 28, 30, 32 of the marker groups.

The image enhancement module 13 for further image processing receives the output data from the output unit 16. The image enhancement module 13 provides a stent enhancement for the stents 34, 36 and at least a part of the sequence of images 24 to provide a stent enhanced image 25.

FIG. 2*e* shows the stent enhanced image 25. Instead of the stents 34 and 36, the stent enhanced image 25 comprises a boosted stent image 54 for stent 34, the stent image 54 providing a boosted image of the stent 34, and a boosted stent image 56 for stent 36. Also, the boosted stent image 56 provides a boosted image of the stent 36.

The boosting may for example be performed by changing the contrast of the images of the stents 34, 36, by bordering the stents 34, 36 in the image 24 of the vasculature structure 38, and/or by changing the color of the stents 34, 36 in the image 24.

The processing unit 14 and the image enhancement module 13 may process the image of vasculature structures 24 in real-time, i.e. on the fly, during a PCI.

The display 22 may display the stent enhanced image 25. The display 22 may then provide a stent enhanced image 25 of which both stents 34, 36 are replaced by the boosted stent images 54, 56, respectively.

Figure 3:
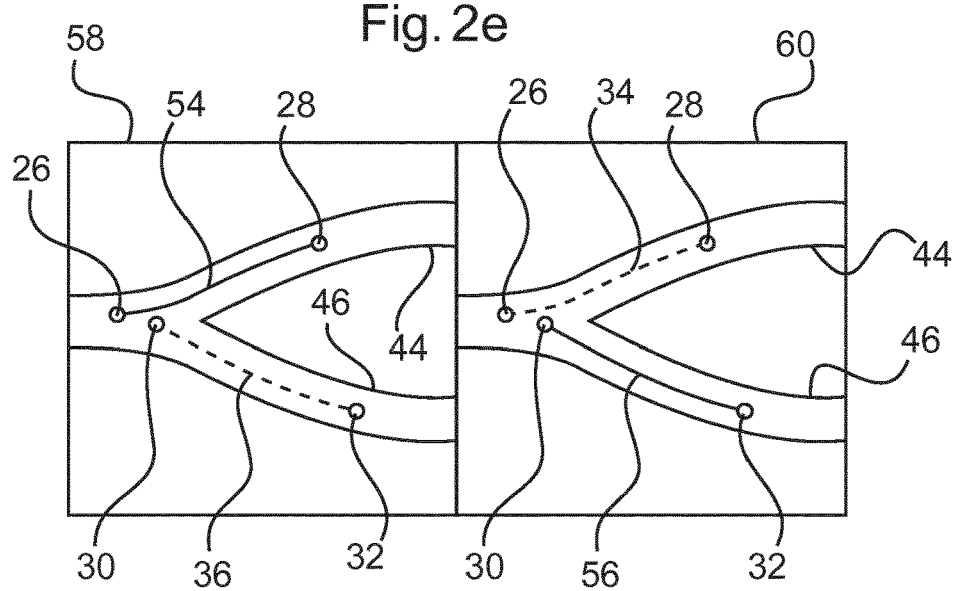
FIG. 3 shows a schematic drawing of separate representations of two stents in an image of vasculature structure.

In another exemplary embodiment shown in FIG. 3, the display 22 may be configured to show 2 images 58, 56, wherein in image 58 only stent 34 is replaced by the boosted stent image 54 and stent 36 is not replaced and wherein in image 60, only stent 36 is replaced by the boosted stent image 56 and stent 34 is not replaced.

FIG. 4 shows an exemplary embodiment of the path indicating elements 64, 66, 74, 76. The image of vasculature structure 24 shown in FIG. 4 comprises wires or guidewires 64, 66 depicted as a line of crosses along the vessel branches 44, 46. The wires or guidewires 64, 66 extend along the vasculature were in one wire or guidewires 64 extends along the vessel branch 44 and the other wire or guidewire 66 extends along vessel branch 46. The wire or guidewires 64, 66 may be used as path indicating elements 64, 66, 74, 76 by the processing unit 14. The wires or guidewires 64, 66 connect the markers 26, 28, 30, 32 in the image of vasculature structure 24. According to FIG. 4, the wire or guidewire 64 connects markers 26 and 28. The wire or guidewire 66 connects markers 30 and 32.

A further exemplary embodiment of the path indicating elements 64, 66, 74, 76 is shown in FIG. 5. FIG. 5 shows a contrast-enhanced image 62 of vasculature structure which may be an angiogram. Before acquiring the contrast-enhanced image 62 of vasculature structure, a contrast agent is introduced into the vessel branches 44, 46. Consequently, the vessel branches 44, 46 are clearly visible and the contrast-enhanced image 62 of vasculature structure. The processing unit 14 may analyze the contrast-enhanced image 62 of vasculature structure to detect the extension of the vessel branches 44, 46 as centerline of the vessel branches 44, 46. Alternatively or additionally, the analysis of the contrast-enhanced image 62 of vasculature structure provides segmented vessel features of the vessel branches 44, 46. The contrasted vessel branches 44, 46 then provide path indicators 74, 76 wherein path indicator 74 denotes a position of a path in the vessel branch 44 and path indicator 76 denotes a position of a path in vessel branch 46.

Figure 6:
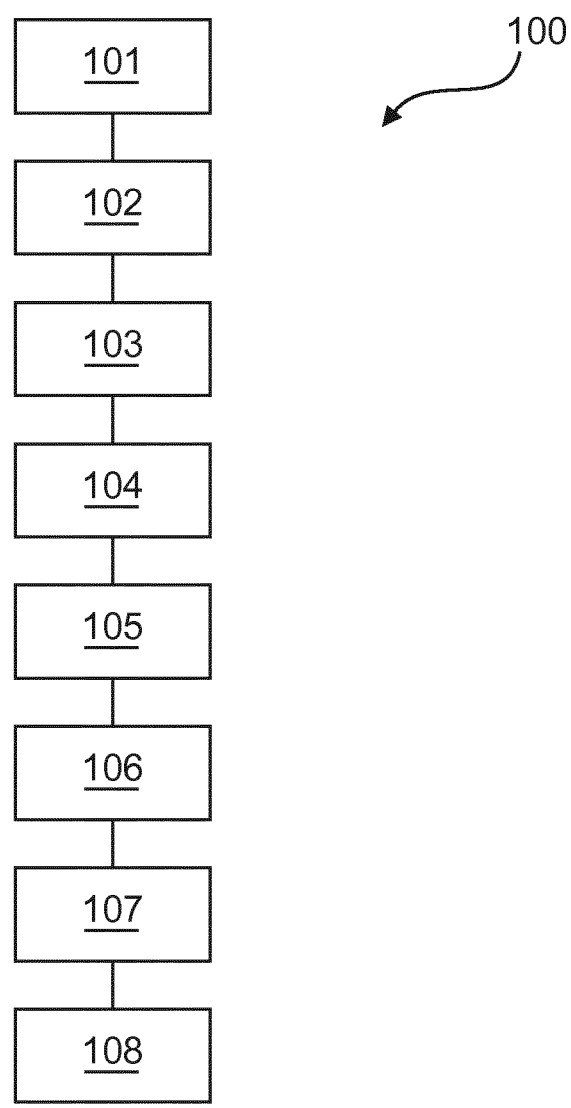
FIG. 6 shows a schematic flowchart of the method.

FIG. 6 shows a flow chart of the method 100 for determining the position of stents 34, 36 in the image of vasculature structure 24.

An image acquisition device may provide 101 a series of image of vasculature structures comprising at least one vessel branch. A device for determining the position of stents in the image of vasculature structure may receive the image of vasculature structure. The images may be received using an input unit of the device. In step a), a processing unit of the device may detect 102 positions of at least two markers for identifying a stent position at least one of the images.

According to step b) at least one path indicator may be detected 103 in at least one vessel branch in at least one of the images. The detection may be performed in a vessel region in which the positions of the markers have been detected before. Moreover, the detection may be performed using the processing unit. The path indicator may for example be a wire or guidewire along the vessel branch according to step b1), for example be a previously acquired position of a separate vessel branch in the vasculature according to step b2), or at least one segmented vessel features with at least one separate vessel branch according to step b3). For the detection of the wire or the guidewire along the vessel branch, an image of vasculature structure may be used, wherein the image of vasculature structure does not comprise a contrast enhancement for the vessels. For the detection of the position of the vessel branch, a contrast-enhanced image of vasculature structure may be analyzed.

According to step c), the at least two markers are associated 104 to the at least one path indicator based on the detected positions of the markers and the location of the at least one path indicator. This means, the positions of the two markers are mapped to the position of the path indicator. If the positions of the markers match the position of the path indicator, this means, that the markers are in the same vessel branch as the path indicator. The association may be performed by the processing unit.

Markers which are associated with the same path indicator are assigned 105 to a marker group in step d). A marker group indicates a position of at least one stent in the vasculature. The assignment may be performed by the processing unit.

The positions of the markers of the marker group may be provided 106 as output data. This means, that the output data indicates that positions of the marker in the marker group. The output data may be provided by an output unit.

That output data may be used to perform 107 the stent enhancement with at least one stent in at least part of the sequence of images. The standard enhancement provides a stent enhanced image. Furthermore, the stent enhancement may be performed with a stent enhancement module.

Furthermore, the stent enhanced image may be received by a display. The display may display 108 the stent enhanced image to a user. The display may display the stent enhanced image as a single image with all stents being enhanced. Alternatively, or additionally, the display may display several stent enhanced images, each stent enhanced image showing a single enhanced stent, wherein the remaining stents are not shown in an enhanced manner. The enhancement of the stents in the stent enhanced imaged may be provided by the change of contrast, a change of color, or by bordering the stent.

The method 100 may be performed on the real-time, i.e. on the fly, during a PCI.

In another exemplary embodiment of the present invention, a computer program or a computer program element 18 being shown in FIG. 1 is provided that is characterized by being adapted to execute the method steps of the method according to one of the preceding embodiments, on an appropriate system.

The computer program element 18 might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium 20 being shown in FIG. 1, such as a CD-ROM, is presented wherein the computer readable medium 20 has a computer program element 18 stored on it which computer program element 18 is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for determining a position of a stent in an image of a vasculature structure, the device comprising:
   input circuitry configured to receive a sequence of images of the vasculature structure comprising at least one vessel branch;
   a processor configured to:
      detect at least two markers associated with the stent in the sequence of images of the vasculature structure and a position of each of the at least two markers;
      detect a path indicator for a vessel branch of the at least one vessel branch in the sequence of images of the vasculature structure and a location of the path indicator;
      associate the at least two markers to the path indicator based on the position of each of the at least two markers and the detected location of the detected path indicator; and
      assign the at least two markers to a marker group based on the association of the at least two markers to the path indicator to indicate position of the stent in the vasculature structure.

2. The device according to claim 1,
   wherein the processor is further configured to:
      detect at least three markers associated with at least two stents in the sequence of images of the vasculature structure and a position of each of the at least three markers;

detect at least two path indicators for at least two vessel branches in the sequence of images of the vasculature structure and a location of each of the at least two path indicators,
wherein the at least two path indicators include a first path indicator and a second path indicator;
associate the at least three markers to the at least two path indicators based on the detected position of each of the at least three markers and the detected location of each the at least two path indicators;
assign one or more markers which are associated with the first path indicator to a first marker group for the first path indicator to indicate position of a first stent in the vasculature structure; and
assign one or more markers which are associated with the second path indicator to a second marker group for the second path indicator to indicate position of a second stent in the vasculature structure.

3. The device according to claim 1,
wherein the processor is further configured to provide stent enhancement of the stent in the sequence of images to provide a stent enhanced image.

4. The device according to claim 3, further comprising:
a display configured to display the enhanced stent image.

5. The device according to claim 1, wherein, to detect the path indicator, the processor is further configured to:
detect, in the sequence of images of the vasculature structure, at least one of a wire or a guidewire that connects the at least two markers as the path indicator.

6. The device according to claim 1,
wherein the vessel branch is a separate vessel branch, and wherein, to detect the path indicator, the processor is further configured to at least one of:
detect the separate vessel branch in the sequence of images of the vasculature structure as the path indicator; or
detect at least one segmented vessel feature for the separate vessel branch in the sequence of images of the vasculature structure as the path indicator.

7. The device according to claim 1, wherein, to detect the path indicator, the processor is further configured to detect, in the sequence of images of the vasculature structure, at least two stent element that extend in a least two different vessel branches and that connect the at least two markers as the path indicator.

8. The device according to claim 7, wherein at least one of the at least two stent elements is a balloon.

9. A system for enhancing stent images in an image of vasculature structure, the system comprising:
the device for determining s position of s stent in an image of the vasculature structure according to claim 1; and
an image acquisition device configured to acquire and provide the sequence of images of the vasculature structure.

10. The system according to claim 9, wherein the image acquisition device is:
an ultrasound device; or
an X-ray image acquisition device.

11. A method for determining the position of a stent in an image of a vasculature structure, the method comprising:
detecting at least two markers associated with the stent in a sequence of images of the vasculature structure and a position of each of the at least two markers;
detecting a path indicator for a vessel branch in the sequence of images of the vasculature structure and a location of the path indicator;
associating the at least two markers to the path indicator based on the detected position of each the at least two markers and the detected location of the path indicator; and
assigning the at least two markers to a marker group based on the association of the at least two markers to the path indicator to indicate a position of at least one stent in the vasculature structure.

12. The method according to claim 11, wherein, detecting the path indicator comprises at least one of:
detecting, in the sequence of images of the vasculature structure, at least one of a wire or a guidewire that connects the at least two markers as the path indicator;
detecting a separate vessel branch in the sequence of images of the vasculature structure as the path indicator; or
detecting at least one segmented vessel feature for the separate vessel branch in the sequence of images of the vasculature structure as the path indicator.

13. A non-transitory computer-readable storage medium having stored a computer program comprising instructions which, when executed by a processor, cause the processor to:
detect at least two markers associated with a stent in a sequence of images of a vasculature structure and a position of each of the at least two markers;
detect a path indicator for a vessel branch of the vasculature structure in the sequence of images of the vasculature structure and a location of the path indicators;
associate the at least two markers to the path indicator based on the detected position of the at least two markers and the detected location of the path indicator; and
assign the at least two markers to a marker group based on the association of the detected at least two markers to the detected path indicator to indicate a position of the stent in the vasculature structure.

14. The method according to claim 11, further comprising:
providing stent enhancement of the stent in the sequence of images to provide a stent enhanced image.

15. The method according to claim 11, wherein detecting the path indicator comprises:
detecting, in the sequence of images of the vasculature structure, at least two stent element that extend in a least two different vessel branches and that connect the at least two markers as the path indicator.

16. The method according to claim 11, further comprising:
detecting at least three markers associated with at least two stents in the sequence of images of the vasculature structure and a position of each of the at least three markers;
detecting at least two path indicators for at least two vessel branches in the sequence of images of the vasculature structure and a location of each of the at least two path indicators;
determining an association of the at least three markers to the at least two path indicators based on the detected position of each of the at least three markers and the detected location of each the at least two path indicators;
assigning one or more markers which are associated with a first path indicator to a first marker group for the first path indicator to indicate position of a first stent in the vasculature structure; and assigning one or more markers which are associated to a second path indicator to a second marker group for the second path indicator to indicate position of a second stent in the vasculature structure, wherein the at least two path indicators include a first path indicator and a second path indicator.

17. The non-transitory computer-readable storage medium according to claim 13, wherein the instructions, when executed by the processor, further cause the processor to:
provide stent enhancement of the stent in the sequence of images to provide a stent enhanced image.

18. The non-transitory computer-readable storage medium according to claim 13, wherein, to detect the path indicator, the instructions, when executed by the processor, further cause the processor to at least one of:
detect, in the sequence of images of the vasculature structure, at least one of a wire or a guidewire that connects the at least two markers as the path indicator;
detect a separate vessel branch in the sequence of images of the vasculature structure as the path indicator; or
detect at least one segmented vessel feature for the separate vessel branch in the sequence of images of the vasculature structure as the path indicator.

19. The non-transitory computer-readable storage medium according to claim 13, wherein, to detect the path indicator, the instructions, when executed by the processor, further cause the processor to:
detect, in the sequence of images of the vasculature structure, at least two stent element that extend in a least two different vessel branches and that connect the at least two markers as the path indicator.

20. The non-transitory computer-readable storage medium according to claim 13, wherein, to detect the path indicator, the instructions, when executed by the processor, further cause the processor to:
detect at least three markers associated with at least two stents in the sequence of images of the vasculature structure and a position of each of the at least three markers;
detect at least two path indicators for at least two vessel branches in the sequence of images of the vasculature structure and a location of each of the at least two path indicators, wherein the at least two path indicators include a first path indicator and a second path indicator;
determine an association of the at least three markers to the at least two path indicators based on the detected position of each of the at least three markers and the detected location of each the at least two path indicators;
assign one or more markers which are associated with a first path indicator to a first marker group for the first path indicator to indicate position of a first stent in the vasculature structure; and
assign one or more markers which are associated to a second path indicator to a second marker group for the second path indicator to indicate position of a second stent in the vasculature structure.

* * * * *